United States Patent

Abrams et al.

[11] Patent Number: 5,960,609
[45] Date of Patent: Oct. 5, 1999

[54] METERING AND PACKAGING METHOD AND DEVICE FOR PHARMACEUTICALS AND DRUGS

[75] Inventors: Andrew L. Abrams, Westport, Conn.; Anand V. Gumaste, Robbinsville, N.J.

[73] Assignee: Microdose Technologies, Inc., Monmouth Jct., N.J.

[21] Appl. No.: 09/097,104

[22] Filed: Jun. 12, 1998

[51] Int. Cl.⁶ ............................................. B65B 1/30
[52] U.S. Cl. ...................... 53/428; 53/111 R; 53/235; 53/467; 53/473; 53/266.1; 53/502; 53/503; 53/900; 141/DIG. 1
[58] Field of Search ................. 198/690.1, 691; 141/DIG. 1; 53/111 R, 235, 266.1, 282, 428, 467, 473, 502, 503, 560, 900, 471

[56] References Cited

U.S. PATENT DOCUMENTS

| | | |
|---|---|---|
| 3,241,625 | 3/1966 | Soojian . |
| 3,437,074 | 4/1969 | Hagopain et al. . |
| 3,889,636 | 6/1975 | Smith . |
| 3,943,437 | 3/1976 | Mourier . |
| 3,999,119 | 12/1976 | Bares . |
| 4,021,587 | 5/1977 | Banker . |
| 4,071,169 | 1/1978 | Dunn . |
| 4,170,287 | 10/1979 | Edwards et al. . |
| 4,204,766 | 5/1980 | Harada . |
| 4,252,434 | 2/1981 | Nakamura et al. . |
| 4,399,699 | 8/1983 | Fujishiro . |
| 4,555,174 | 11/1985 | Kramer . |
| 4,594,901 | 6/1986 | Norman . |
| 4,848,267 | 7/1989 | Slayton et al. . |
| 4,878,454 | 11/1989 | Cann . |
| 5,005,516 | 4/1991 | Speer . |
| 5,102,045 | 4/1992 | Diana . |
| 5,204,055 | 4/1993 | Sachs et al. . |
| 5,214,386 | 5/1993 | Singer et al. . |
| 5,454,271 | 10/1995 | Yamamoto et al. . |
| 5,490,962 | 2/1996 | Cima et al. . |
| 5,699,649 | 12/1997 | Abrams et al. . |

FOREIGN PATENT DOCUMENTS

| | | |
|---|---|---|
| 0431924 | 1/1996 | European Pat. Off. . |
| 9800337 | 1/1998 | WIPO . |

OTHER PUBLICATIONS

Science News, vol. 151, p. 205, "Ink jets not just for the printed page". Apr., 1997.
Japanese Patent Abstract 4,277,126 Oct., 1992.

*Primary Examiner*—Daniel B. Moon
*Attorney, Agent, or Firm*—Hayes Soloway Hennessey Grossman & Hage PC

[57] ABSTRACT

Electrostatic phototechnology is used to package microgram quantities of fine powders such as drugs in discrete capsule and tablet form. An electrostatic "image" having a given size and charge density is exposed to ionized drug powder to attract a known amount of drug to the image. The resultant drug "image", is then transferred to a an open ended capsule, a partially formed tablet or edible wafer or belt. The capsule is then sealed, i.e. by capping, or the tablet finished.

35 Claims, 10 Drawing Sheets

- 18A — HOLDING CHAMBER
- 16A
- 20A — TO METERING CHAMBER
- IONIZATION CHAMBER
- HIGH VELOCITY JET STREAM
- DEAGGREGATION & AEROSOLIZATION CHAMBER

FIG. 8
PRIOR ART

- ELECTROSTATIC PLATE FOR AEROSOLIZATION
- DEAGGREGATION & AEROSOLIZATION CHAMBER
- 18B
- 20B — TO METERING CHAMBER
- BULK DRUG RESERVOIR
- 16B
- IONIZATION CHAMBER
- HIGH FREQUENCY VIBRATOR

FIG. 9
PRIOR ART

PERCENTAGE OF SUSPENDED PARTICLES vs. TIME

METERING AND PACKAGING METHOD AND DEVICE FOR PHARMACEUTICALS AND DRUGS

BACKGROUND OF THE INVENTION

The present invention relates to the packaging of dry powders and particularly to the metering and packaging of precise quantities of pharmaceuticals and drugs for medical uses. The invention has particular utility in the metering and packaging of dry powders, particularly very small amounts of dry powder pharmaceuticals and drugs, and will be described in connection with such utility, although other utilities are contemplated.

The certification of new pharmaceuticals is a lengthy and costly process involving animal studies followed by chemical trails to establish both efficacy and safety. Because a pharmaceutical's characteristics may be affected by changes in manufacturing and/or packaging, the approval process limits the approval to a particular manufacturing and packaging process.

In our earlier U.S. Pat. No. 5,699,649, granted Dec. 23, 1997, we describe a method and apparatus for packaging microgram quantities of fine powders such as pharmaceuticals using electrostatic phototechnology techniques. More particularly, as described in our aforesaid U.S. Pat. No. 5,699,649, the ability of powders to acquire an electrical charge advantageously is utilized for precisely measuring exact microgram quantities of the powder, whereupon these exact microgram quantities are then placed in individual containers, and the containers sealed.

Electrostatic charge has been employed to attract a given quantity of powder to a surface. An example of this is the laser printer or the electrostatic copy devices where a drum is charged and toner particles are attracted and held in position by the charge. The charge on the drum is neutralized by the attracted toner powder, thus limiting the amount of toner in accordance with the charge image on the drum. The charge on these printer drums is then transferred to a sheet of paper or other carrier to give a final image. In our U.S. Pat. No. 5,699,649, the same electrostatic charge technology is employed for transferring a predetermined amount of a finely powdered pharmaceutical or drug to a carrier or an intermediate such as a drum, carrying a charge of predetermined intensity and area, rotating the charged drum surface, carrying the predetermined amount of powdered pharmaceutical or drug on its surface, to a transfer station where the charge is overcome and the dry powder is transferred to a package which is then sealed. In lieu of a drum, a belt, or other movable surface is charged to a given potential in a localized area.

When a given amount of a powdered pharmaceutical or drug is to be packaged, the charge and area of charge can be determined experimentally for each dose of pharmaceutical or drug and each particle size distribution. This can be done by controlling either the charged area for a given charge density or the total electrostatic charge on any individual charged area. These conditions can be adjusted to provide essentially the exact desired amount of the particular pharmaceutical or drug to be transferred at the transfer station.

BRIEF DESCRIPTION OF THE INVENTION

In the present invention, the electrostatic charge technology described in our aforesaid U.S. Pat. No. 5,699,649 is adopted to be used for measuring and packaging unit doses of a pharmaceutical or drug in a readily ingestible form, i.e. as a tablet or capsule. The technology thus described permits reproducible precise measurement and packaging of a pharmaceutical or drug, and which may be scaled from laboratory to pilot plant to full scale production without the need for recertification.

BRIEF DESCRIPTION OF THE DRAWINGS

Further features and advantages of the present invention become apparent from the following detailed description of the invention, taken in conjunction with the accompanying drawings wherein like numerals depict like parts, and wherein:

FIG. 1 shows a schematic representation of the attraction of negatively charged powder particles to a support having a positive charge on the surface thereof;

FIG. 2 shows a block diagram of the various steps involved in practicing the invention;

FIG. 3 is a schematic representation of one form of drum type electrostatic device for transferring given small quantities of powdered drugs from an electrostatic attraction station, where a given quantity of powdered drug is attracted to and neutralizes a given charge on the drum, and a subsequent transfer station where the drug is transferred from the drum to a package therefor;

FIGS. 4 and 5 are schematic functional representations of preferred components employed in the FIG. 3 type of apparatus;

FIG. 6 shows a different system wherein separate carriers, having micronized drug particles electrostatically attached to their surface, are used to carry the drug to the charged transfer surface;

FIGS. 7 and 8 show methods of aerosolizing the powdered drug and ionizing the drug to give it a specific charge;

FIG. 9 shows a graph illustrating the percentage of suspended particles as a function of time and size, permitting creation of a suspended particle stream of any given desired size distribution;

FIG. 10 shows another embodiment of applying the aerosolized drug to a drum carrying charge "image";

FIG. 11 illustrates an ion projection system for creating the charge "image" on a dielectric surface;

FIG. 12 is a view similar to FIG. 2, and illustrating an alternative embodiment of the invention;

FIG. 13 is a view similar to FIG. 2, and illustrating another alternative embodiment of the invention;

FIG. 14 is a view similar to FIG. 2, and illustrating yet another alternative embodiment of the invention; and FIG. 15 is a view similar to FIG. 2, and illustrating still yet another alternative embodiment of the invention.

DETAILED DESCRIPTION OF THE INVENTION

Referring first to FIG. 1 there is illustrated a chamber 14 containing aerosolized dry powder particles of a pharmaceutical or drug 10. These particles 10 are suspended in air and carry a charge, for example a negative charge. Also in the chamber is a support surface 12 having a charge opposite to that on the particles. The support surface 12 will attract a number of charged particles 10 sufficient to neutralize the charge on the surface of the support 12. This support surface is one that can hold a discrete electrical charge on its surface, such as insulating material, e.g. plastic or a semiconductor material, such as selenium, used in the photocopy industry.

The actual amount of pharmaceutical or drug powder transferred to the carrier sheet is a function of the mass-tocharge ratio of the powdered particles. If one assumes surface charge saturation, the amount of charge carried by the particles is directly related to the surface area. For spheriodal particles, the charge varies as the square of the radius and the mass varies as the cube. Thus, the amount of charged particles picked up by a given portion of the surface of the charge carrier will be a function the total charge on the carrier. Thus, with a given surface charge density on the carrier, the amount of pharmaceutical or drug powder picked up is directly proportional to the charged area. Thus, for doubling the amount of pharmaceutical or drug powder to be picked up, and thus the dose amount, the area on which charge is placed can be doubled. This can be used as a basic method to control the amount of powder to be picked by the carrier. Thus, for any particular powder or particle size distribution of powder, the exact area and amount of charge needed can be experimentally determined.

Figure 2:
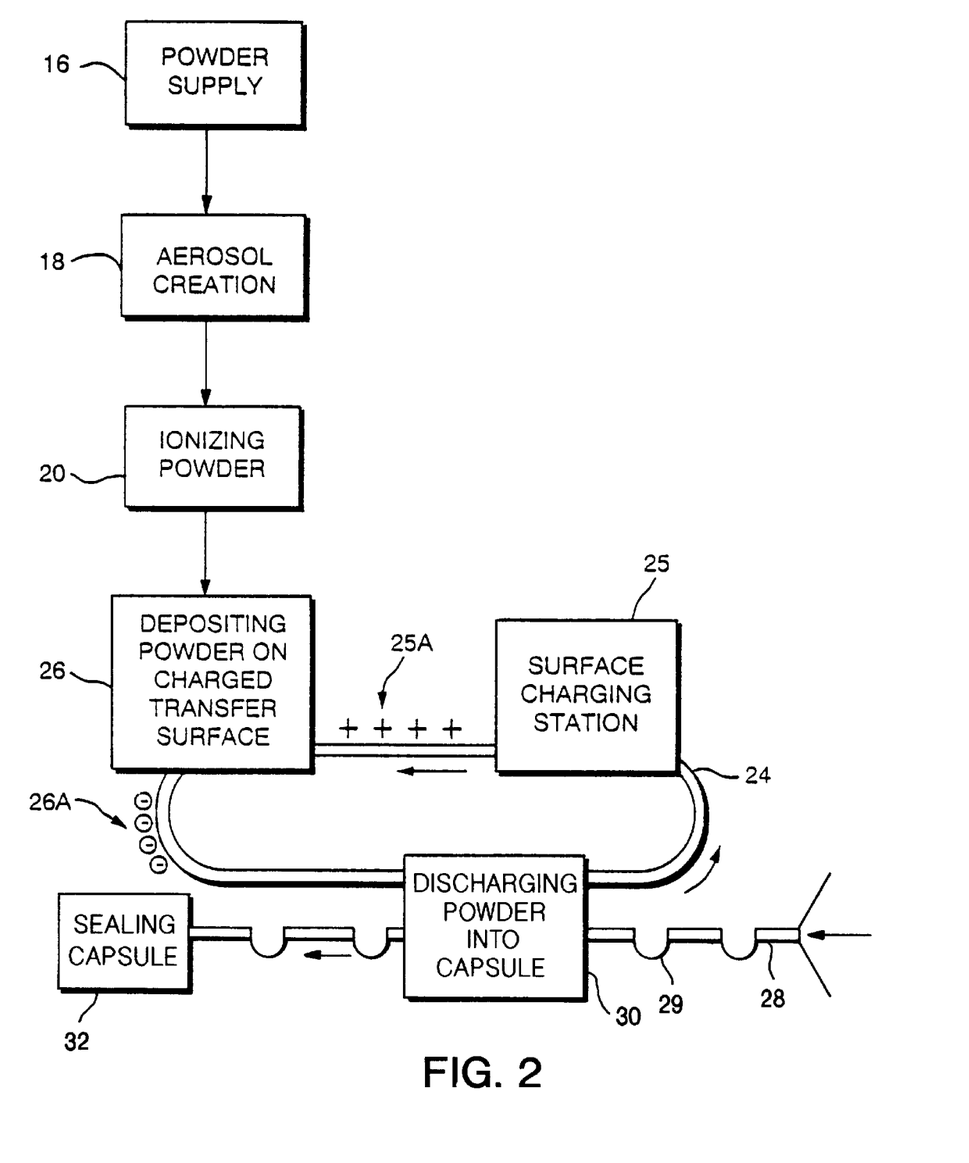

Referring now to FIG. 2, there is a schematic flow diagram of the various items of equipment needed to perform in the total process from powder supply to packaged pharmaceutical or drug, i.e. in capsule form, containing a specified amount of pharmaceutical or drug powder in the package. At 16 is indicated the pharmaceutical or drug powder supply which is fed into a device 18 for creating an aerosol of the powder. Next the powder particles are ionized at 20. As will be indicated later, a number of these steps and pieces of equipment can be combined. At 24 is indicated a carrier surface capable of maintaining a space charge on its surface. This can be a plastic belt, for example, or a selenium drum of the type used in Xerox™ photocopiers. This carrier surface 24 is passed through a charging station 25 where a predetermined electrostatic charge 25A (an electrostatic "image") is created on a predetermined area of the transfer surface. This charged surface 25A then passes through a step 26 wherein powder is deposited on the carrier surface in a sufficient amount 26A to neutralize the charge carried by the carrier surface. Thereafter, the carrier surface, carrying the predetermined amount 26A of powder on its surface, is passed to a powder discharging device 30 which discharges the powder 26A from the surface 24 into the open end of a capsule 29, which capsule is carried on a conveyor belt 28. A carrier 24 and conveyor belt 28 are indexed and synchronized in a predetermined manner so that the electrostatic "image" aligns directly over the open end of capsule 29 and powder discharging device 30 during the discharge sequence. At that time powder discharging device 30 is activated whereupon the predetermined amount 26A of powder is released from surface 25A, and falls into capsule 29. The capsule 29 containing its charge of powder 26A, then passes through a capsule sealing step 32 wherein the capsule is capped.

Figure 1:
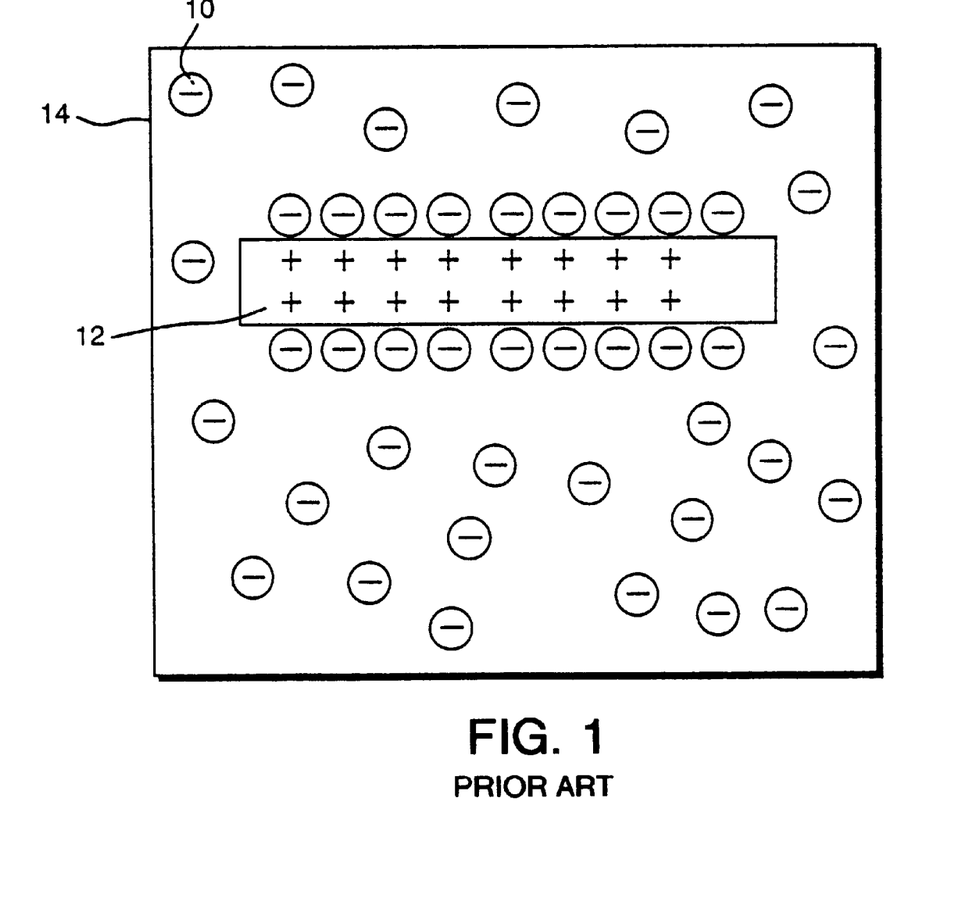

As mentioned previously in discussing FIG. 1, the carrier surface with the electrostatic charge carries a known amount of charge on its surface and the polarity of this charge is opposite to that of the powder particles suspended in the chamber. The charged particles migrate to the charged surface because of the attraction by the opposite nature of the charges. This migration of the particles continues until the charge on the carrier surface is neutralized.

The actual amount of powder mass transferred to the carrier surface is a function of the mass-to-charge ratio of the charged particles. Although it is difficult to achieve a linear relationship between the mass and the actual charge, it is possible to establish a fixed relationship between the surface area of the powder particles and the charge the powder particle is carrying at charge saturation. However, the surface area of a mixed group of powder particles of different sizes and shapes can be extremely difficult to calculate mathematically, particularly when the shapes are irregular, (e.g. non-spherical, microcrystalline, etc.) As mentioned earlier, the simplest method of determining the amount and area of charge to attract a given weight of particles is to estimate the correct area and charge and then apply the estimated charge to the estimated area on the carrier surface 24 and expose this selectively charged area to a mass of powder which has been ionized in the ionizing step. The amount of powder deposited can then be readily measured at the discharge step. Thereafter, either the size of the charged area or the amount of charge applied to the area at the charging station 25 can be adjusted upwardly or downwardly to provide the correct amount of charge, both in area and charge intensity, for picking up a desired weight of oppositely charged powder.

Figure 3:
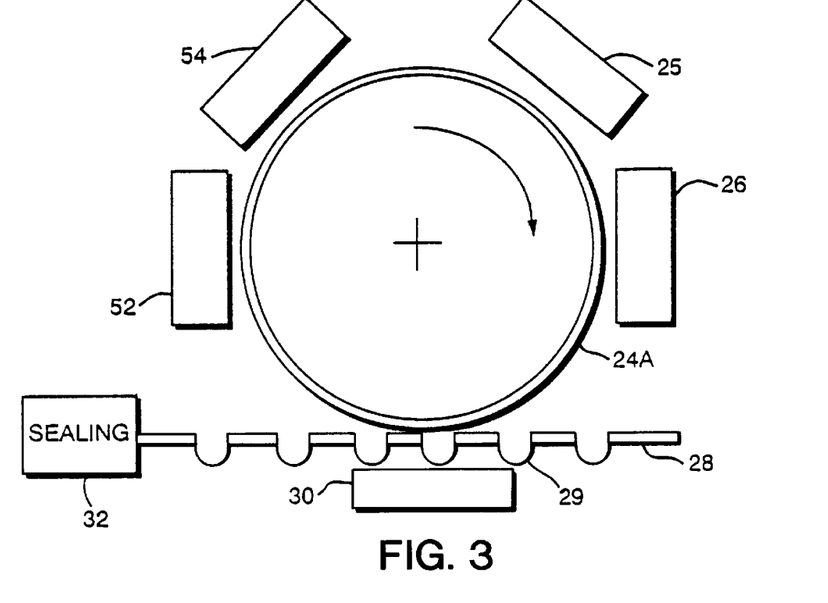
Figure 4:
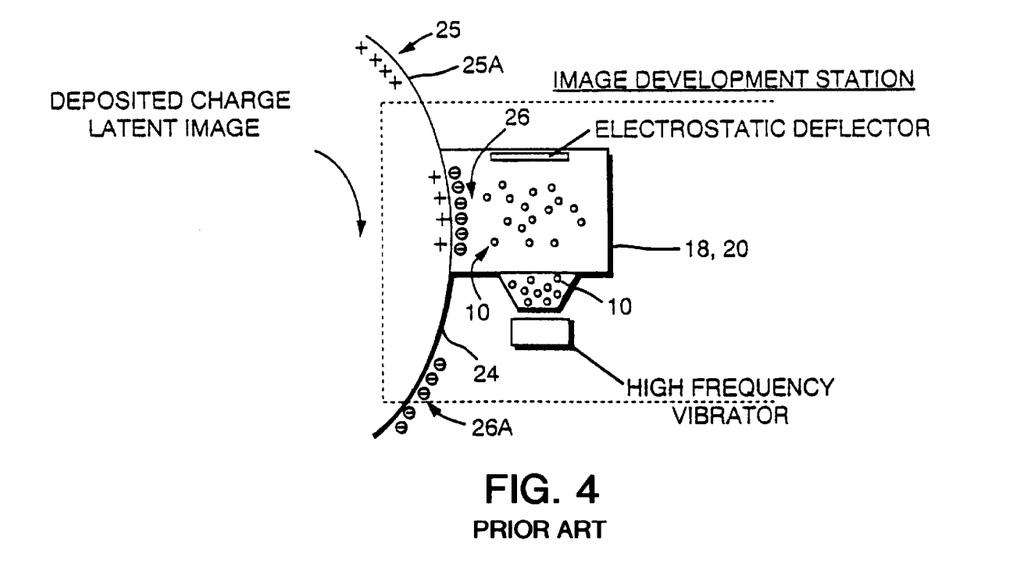
Figure 5:
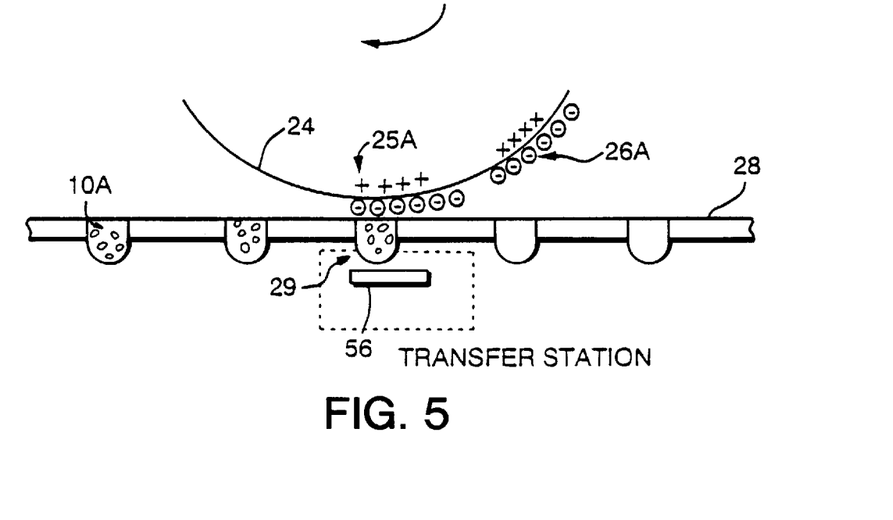

Referring now to FIGS. 3, 4, and 5 one preferred apparatus for accomplishing the invention is illustrated schematically in FIG. 3, with details of the components thereof being shown in FIGS. 4 and 5. The charge carrying surface is illustrated as a photo sensitive drum 24A which rotates between the charge "image" exposure 25 which creates a charge "image" 25A on the surface of the drum 24A. (see FIG. 4) This "image" exposure can be a light source e.g., a laser beam (or other controllable photon source), which is capable of creating an electrostatic "image" 25A on the surface of the drum of a desired size and charge density. The charge "image" 25A is then rotated to the image development station containing an ionized cloud of drug powder which is attracted to the charge "image" 25 to neutralize charge in the "image", thus, forming a powder "image" 26A containing a predetermined amount of powder. (see FIGS. 4 and 5) This powder "image" 26A is rotated to a drug transfer station 30 where it is released into the open ended capsule 29 carried on belt 28. This transfer to the capsules 29 is accomplished, in one preferred embodiment, by the use of high voltage plate 56 (see FIG. 5) which overcomes the attraction of the charged "image" 25A on the surface of the drum, thus releasing the powder "image" 26A into the capsule 29. The pocket containing the predetermined quantity of drug is then passed through the capsule capping step 32.

Figure 6:
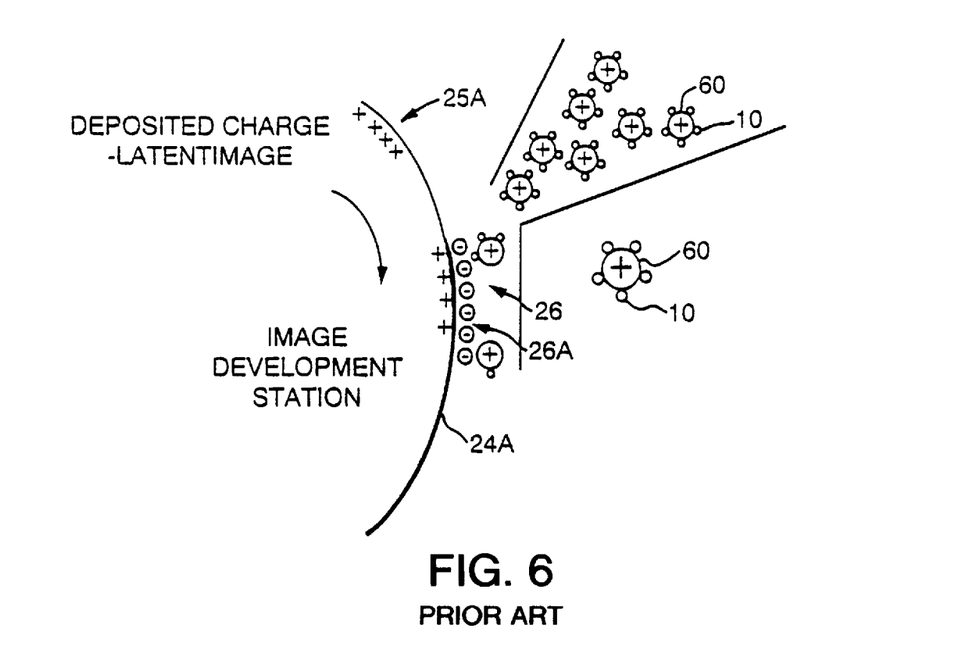

FIG. 6 shows another embodiment of the invention wherein the micronized drug particles 10 are carried on the surface of discrete carriers 60 which can be, for example, small plastic beads, for example. When these plastic beads are contacted with an image 25A, the micronized particles 10 are transferred to the charge "image" 25A on the surface of the drum 24A from the discrete carriers 60. To accomplish this, the positive charge on the image 25A should be higher than the positive charge on the surface of the individual carriers 60.

Figure 7:
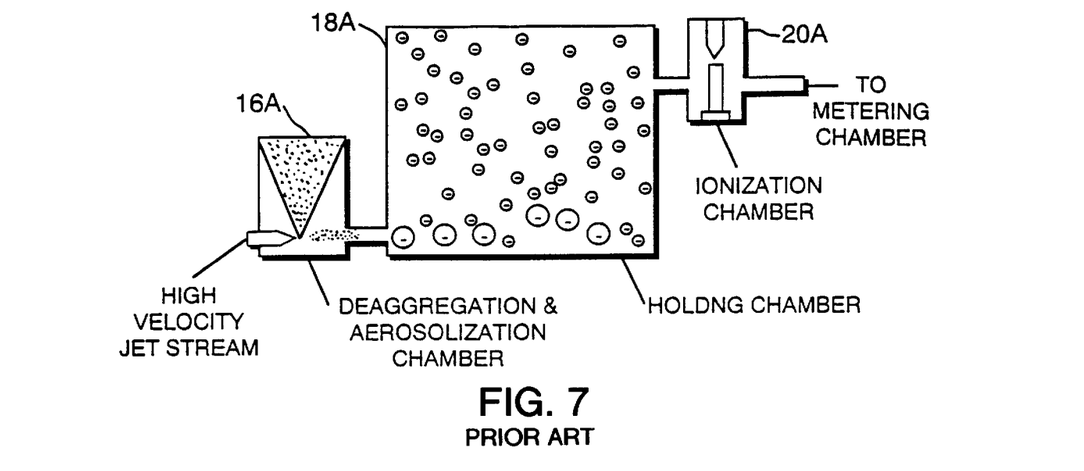
Figure 8:
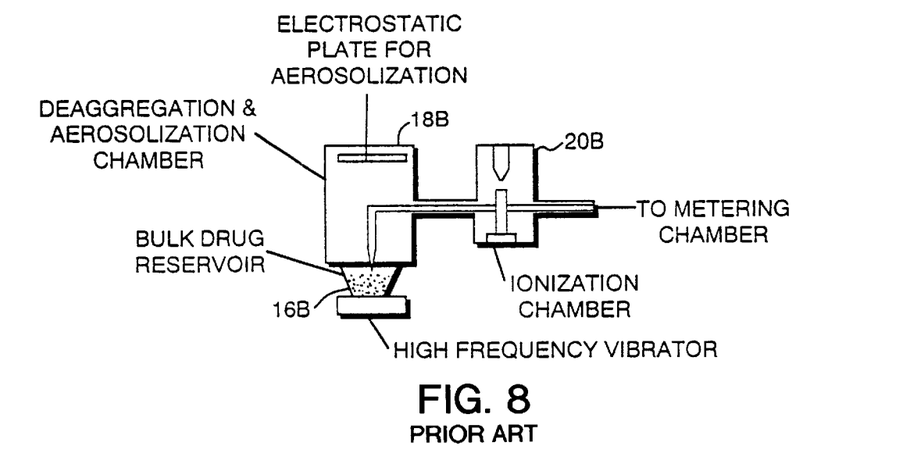
Figure 9:
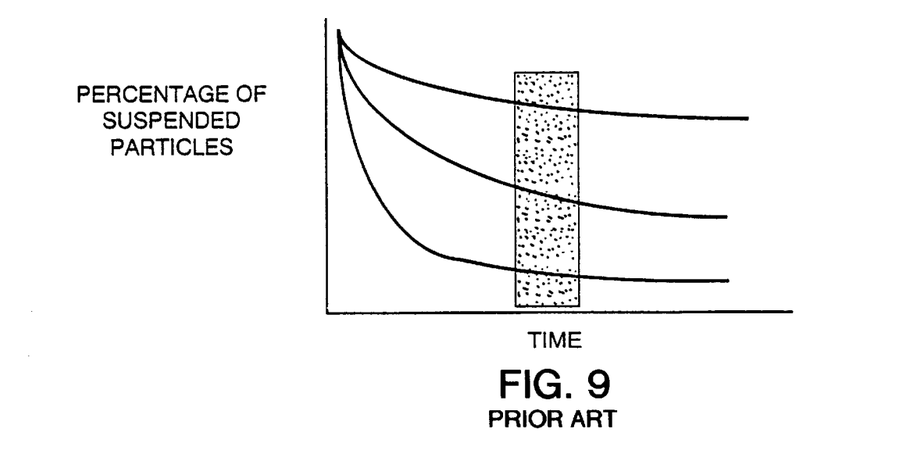
Figure 10:
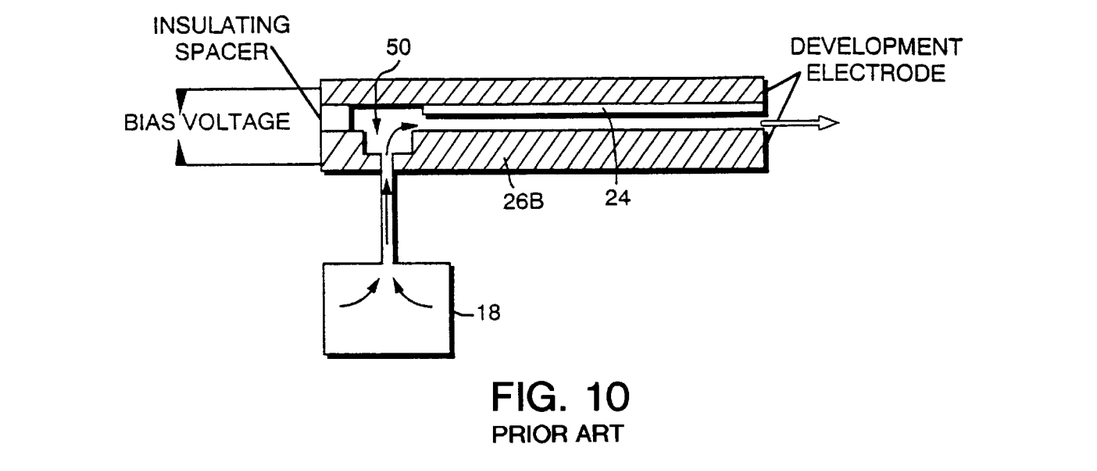
Figure 11:
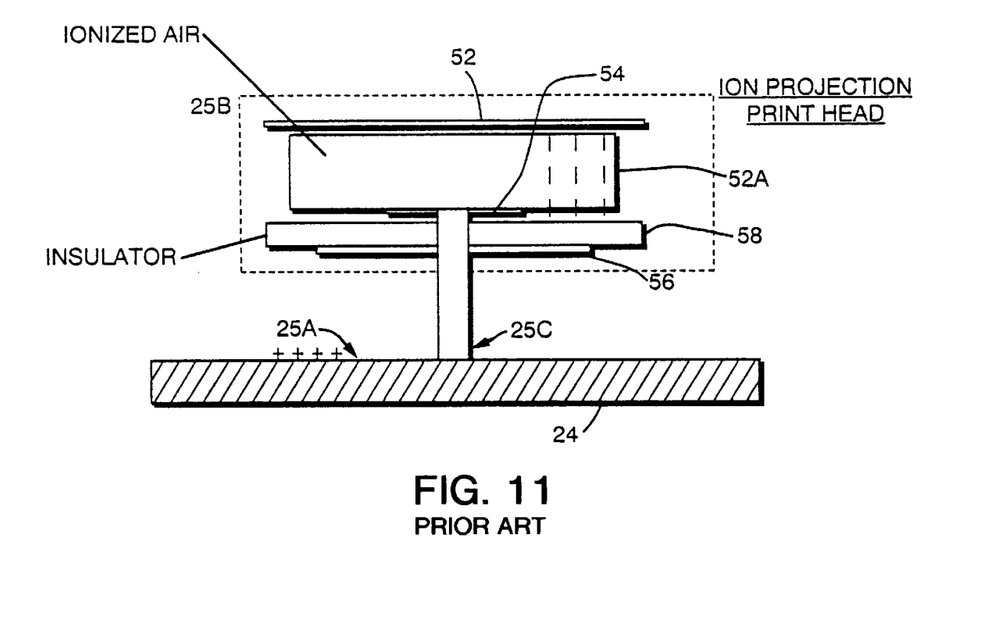
Figure 12:
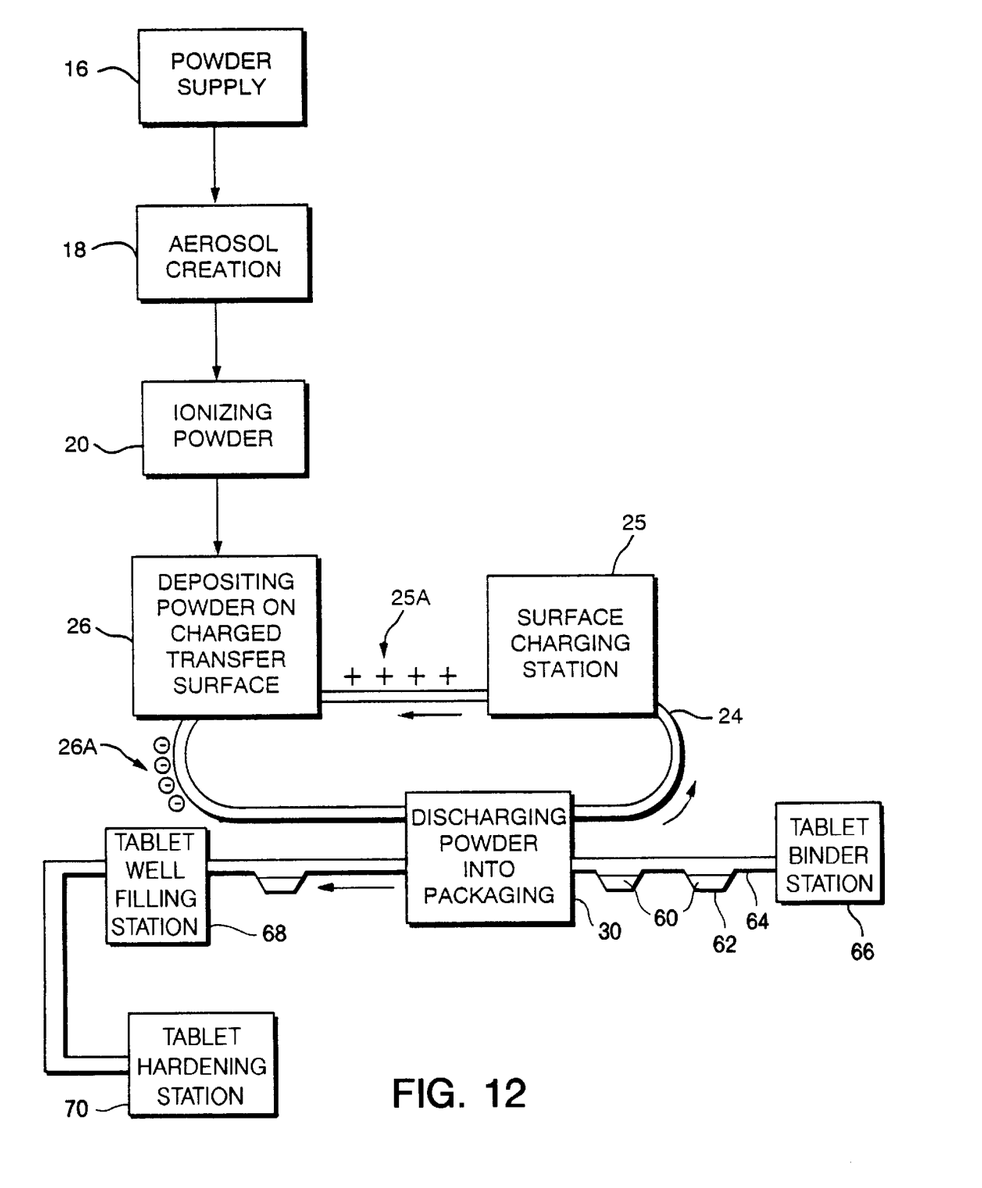
Figure 13:
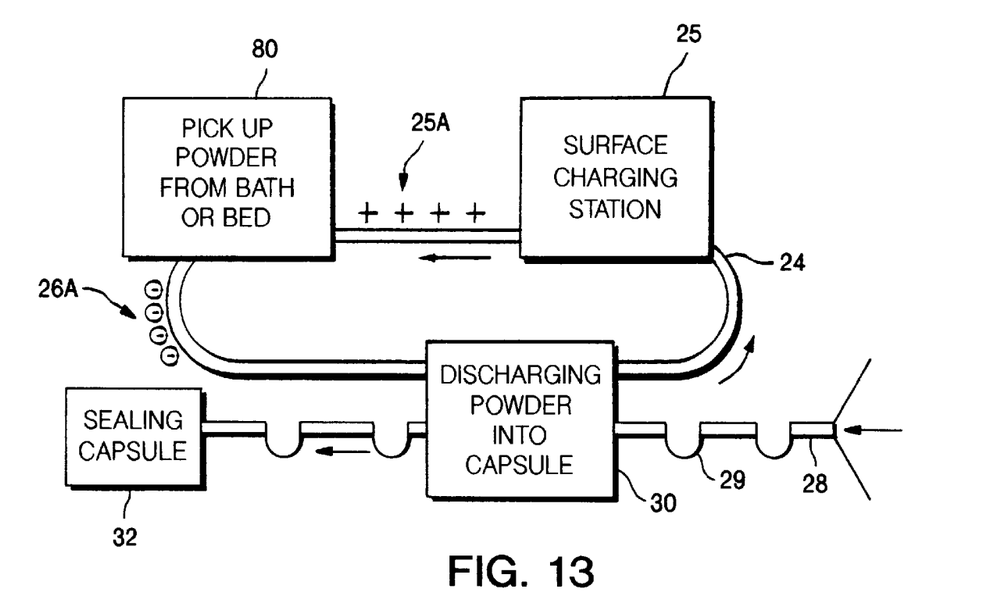

FIGS. 7 and 8 show additional details of means for both handling drugs and providing aerosolization and ionization to provide a suspended stream of fine drug powders having a predetermined size and charge. In FIG. 7 and 8, elements 16A, 18A and 20A and 16B, 18B and 20B correspond to the equivalent elements in FIGS. 2, 3 and 4.

Since repeatability is important for drug metering it is necessary to effectively address the issue of charge-to-mass variation with particle size. One method of over-coming this problem is to control the particle size distribution in the drug powder. FIG. 8 shows one implementation to achieve this control of particle size. The voltage on the electrostatic deflector is adjusted to control the particle sizes to be suspended in the holding chamber for delivery to the ionization chamber. Once the desired particle sizes are suspended they are drawn into the ionization chamber to ensure surface charge saturation on the particles. This will give a known charge to the mass ratio.

FIG. 7 shows an alternative means for controlling the size distribution. A high velocity air stream is used to deaggregate the powder. The deaggregated powder is then contained in holding chamber 18A. The purpose of the holding chamber is to allow the larger size particles to settle, thereby producing a favorable particle size distribution. The particle size distribution is a function of the holding time as shown in FIG. 9. The suspended particles are then ionized and exposed to the charge image as shown at 26 in FIG. 3.

FIG. 9 shows the percentage of particles sizes suspended in a holding chamber as a function of time. Such a chamber may be provided with a slow upward flowing air current to maintain the aerosol suspension. As can be seen, the percentage of suspended particles is very largely determined by particle size. Through experiment one can select a time slot that will give the desired particle size distribution for any particle drug dosage. Additionally, or in place of settling time, one or more filters can be used for obtaining a given particle size range.

FIG. 10 is similar to FIG. 4 except that the Image Development Station 26A in this Figure is replaced with a stationary electrode 26B and an air passageway 50 for carrying the aerosolized powder. The rotating drum has a dielectric or photoreceptor surface 24 on to which is deposited the latent image. As an example the aerosolization chamber would be similar to that shown in FIG. 7. The metering chamber in FIG. 7 is then the air-passageway 25 between the dielectric surface 24 and the stationary electrode 26B. The undeposited powder then exits at the right side of this air-passageway to be collected for later use or recirculated back into the aerosolization chamber.

FIG. 11 above shows an ion projection print head where an ion beam is used to produce a charge "image" on a dielectric surface. The corona wire 52 has a high voltage applied to it which causes the air to breakdown and produces the ions 52A necessary for the operation of the ion projection printers. The remainder of the ion projection print head includes the usual control electrode 54, screen electrode 56 and insulator 58. The relative potential that is applied to the control and screen electrodes then regulates the amount of ions 25C that will be metered and deposited on to the dielectric surface 24 these ions being deposited on the surface to form the latent image 25A. Both the intensity and size of the ion beam can be adjusted as will be apparent to one of ordinary skill in the art. The advantage of this system is that it does not require a photosensitive surface and can therefore be rugged making it suitable for the manufacturing environment.

The invention is susceptible to modification. For example, the invention advantageously may be employed to form tablets each containing a precise amount of pharmaceutical or drug. FIG. 12 is similar to FIG. 2. However, in the FIG. 12 embodiment, tablet binder material 60 is deposited in wells 62 of belt 64 at a first depositing station 66. The belt 64 carrying the partially filled wells 62 is then passed into powder discharging device 30, where the belt is indexed, as before, in coordination with carrier surface 24. The predetermined amount 26A of powder is then discharged from surface 24 into well 62, whereupon the belt is then moved to a well filling station 68 where the wells 62 are filled. Well filling station 68 may include a doctor blade (not shown) or the like, for topping the wells 62. Thereafter the filled wells pass through a tablet hardening station 70 wherein the tablets are formed into unitary masses in known manner.

FIG. 13 illustrates another alternative embodiment of the invention, in which the surface of the drum 24 bearing the charged "image" 25A is passed through a powder bath or fluidized bed 80 containing the powder particles. As before, the powder particles will stick only to the charged area on the surface of the drum.

Referring to FIG. 14, in yet another embodiment of the invention, a transport belt 82 carries a plurality of spaced edible wafers 84 or the like upon which the predetermined amount of powder 86 may then be discharged onto the individual wafers.

Referring to FIG. 15, in yet another embodiment of the invention, transport belt 82 carries tape or sheet 88 formed of an edible substrate such as starch. The powder particles 90 are deposited uniformly on the sheet 88, which is then stripped from the belt 82, and cut into specific sizes to determine the dose.

As can be seen from the foregoing description, the present invention permits metering and packaging of dry powder pharmaceuticals and drugs, in a highly precise, reproducible manner. Moreover, the invention readily may be scaled from laboratory, i.e desk top size, to pilot plant to full scale production capacity by simply changing size and/or handling speed. Since all units operate according to identical processes, the drug used for clinical trials would have the same manufacturing process as in full scale production. Thus, production certification may be simplified.

Another advantage of the present invention is that the system may be employed to meter and deposit different drugs and/or different dosages by simply changing the "image". Alternatively, dosages may be changed, e.g. larger doses made, by advancing the belt in a stepwise manner so that two or more printed "dots" or a printed line may be deposited at one site on the belt. The belt may then be advanced, and the process continued. Still other modifications are possible. For example, the invention advantageously may be used for "printing" diagnostic reagents or the like on a carrier or substrate.

Still other modifications and variations of the invention described herein may be made and are intended to come within the scope of the appended claims.

We claim:

1. The method of packaging dry powder pharmaceuticals, drugs and reagents comprising the steps of developing a predetermined electrostatic charge having a predetermined "image" area on a powder carrier surface, contacting said carrier surface with a sufficient amount of powder to neutralize said charge, whereby to isolate a predetermined quantity of powder, moving said isolated quantity of powder and said surface to a transfer station, transferring said isolated quantity of powder to a partially formed discrete package carried on a transport belt, whereby to form a discrete packaging containing said predetermined amount of powder.

2. A method according to claim 1, wherein said partially formed package comprises an open-ended capsule, including the step of sealing said capsule by capping.

3. A method according to claim 1, wherein said partially formed package comprises a partially formed tablet, and including the step of completing formation of said tablet after transferring said powder thereto.

4. The method of claim 1, wherein said predetermined charge and area on said carrier surface are estimated, said estimated electrostatically charged area is then exposed to said powder of opposite charge and the amount of powder attracted to said predetermined area is measured, thereafter necessary adjustments to the amount of charge and/or the area is made to attract the predetermined desired amount of powder to said "image" area.

5. The method of claim 4, wherein a high velocity air stream is used to deaggregate and aerosolize the powder particles and a holding chamber is used to control the particle size distribution in the air stream using particle settling times.

6. The method of claim 4, wherein the charge "image" is produced by an ion beam whose intensity and/or area can be varied.

7. The method of claim 4, wherein the charge "image" is produced by a photon beam whose intensity and/or area can be varied.

8. The method of claim 4, wherein means are provided for controlling particle size distribution of particles in the powder deposited on the charge "image".

9. The method according to claim 1, wherein said powder carrying surface and said transport belt are synchronized to move together.

10. The method according to claim 1, wherein said partially formed package comprises an edible wafer.

11. The method of packaging dry powder pharmaceuticals, drugs and reagents comprising the steps of developing a predetermined electrostatic charge having a predetermined "image" area on a powder carrier surface, contacting said carrier surface with a sufficient amount of powder to neutralize said charge, whereby to isolate a predetermined quantity of powder, moving said isolated quantity of powder and said surface to a transfer station, transferring said isolated quantity of powder to a transport belt, and dividing said belt to form discrete packages each containing a predetermined amount of powder.

12. A method according to claim 11, wherein said transport belt comprises an edible material.

13. A method according to claim 12, wherein said powder carrier surface comprises a separate element carried on said belt, and including the step of stripping said separate element from said transport belt.

14. The method according to claim 13, wherein said separate element comprises an edible material.

15. The method according to claim 14, wherein said edible material comprises starch.

16. The method of claim 11, wherein said predetermined charge and area on said carrier surface are estimated, said estimated electrostatically charged area is then exposed to said powder of opposite charge and the amount of powder attracted to said predetermined area is measured, thereafter necessary adjustments to the amount of charge and/or the area is made to attract the predetermined desired amount of powder to said "image" area.

17. The method of claim 16, wherein a high velocity air stream is used to deaggregate and aerosolize the powder particles and a holding chamber is used to control the particle size distribution in the air stream using particle settling times.

18. The method of claim 16, wherein the charge "image" is produced by an ion beam whose intensity and/or area can be varied.

19. The method of claim 16, wherein the charge "image" is produced by a photon beam whose intensity and/or area can be varied.

20. The method of claim 16, wherein means are provided for controlling particle size distribution of particles in the powder deposited on the charge "image".

21. The method according to claim 16, wherein said powder carrying surface and said transport belt are synchronized to move together.

22. The method according to claim 11, wherein said transport belt comprises an edible material.

23. The method according to claim 22, wherein the edible material comprises starch.

24. Apparatus for packaging for powder comprising:

a source of powder, a powder carrier surface;

means for applying a predetermined electrostatic charge to a predetermined area of said carrier surface, to create a charge "image" on said surface, means for applying to said powder an electrostatic charge opposite to that of said electrostatic charge on said carrier surface;

means for exposing said charged area of said area on said carrier surface to charged powder to create a powder "image" on said carrier surface, means for transferring said powder adhering to said carrier surface to a transfer system and neutralizing said electrostatic charge on said carrier surface to cause the powder to transfer into a discrete, package, carried on a transport belt.

25. The apparatus according to claim 24, wherein said package comprises a partially formed package, and including means for sealing said discrete, partially formed package.

26. The apparatus of claim 25, wherein said partially formed package comprises open capsules, and wherein said means for sealing said partially formed package comprises a capsule sealing station.

27. The apparatus of claim 25, wherein said partially formed package comprises partially formed tablets, and said means for sealing said partially formed tablet comprise means for finish forming said tablets.

28. The apparatus of claim 24, wherein the means for placing the electrostatic "image" on the carrier surface is adjustable both in intensity and area so that the exact amount of electrostatic charge and area thereof can be controlled.

29. The apparatus of claim 24, which additionally includes a means to control the powder particle size distribution to ensure repeatability and accuracy of powder metering.

30. The apparatus of claim 24, wherein a high frequency vibrator such as a piezo crystal, electromagnetic, mechanical or other means is used to deaggregate the powder and an electrostatic potential is used to aerosolize the particle size distribution of interest.

31. The apparatus of claim 24, wherein the charge "image" is produced by an ion beam whose intensity and/or area can be varied.

32. The apparatus of claim 24, wherein the charge "image" is produced by a photon beam whose intensity and/or area can be varied.

33. The apparatus of claim 24, and including means for indexing movement of said powder carrier surface and said transport belt.

34. The apparatus of claim 33, and further including means for activating said transfer system to neutralize said electrostatic charge when said transport belt and said carrier surface are in predetermined position relative to one another.

35. The apparatus of claim 24, wherein said powder is transferred onto an edible sheet carried on the transport belt, and including means for dividing said edible sheet into discrete packages.

* * * * *